United States Patent [19]

Giuseppe et al.

[11] Patent Number: 5,744,127
[45] Date of Patent: Apr. 28, 1998

[54] DERIVATIVES OF BENZOXAZOLE USEFUL AS UV FILTERS

[75] Inventors: Raspanti Giuseppe; Zanchi Giorgio, both of Bergamo, Italy

[73] Assignee: 3V Inc., Weehawken, N.J.

[21] Appl. No.: 710,777

[22] Filed: Sep. 20, 1996

[51] Int. Cl.$^6$ ............ C07D 251/54; C07D 263/57; A61K 7/42

[52] U.S. Cl. ............ 424/59; 424/60; 424/401; 514/245; 544/196; 544/197; 544/198

[58] Field of Search ............ 424/59, 60; 514/245; 544/198, 196, 197

[56] References Cited

U.S. PATENT DOCUMENTS

| | | | |
|---|---|---|---|
| 3,696,193 | 10/1972 | Guglielmetti et al. | 424/59 |
| 5,332,568 | 7/1994 | Raspanti | 424/59 |
| 5,372,805 | 12/1994 | Finkel et al. | 424/59 |
| 5,393,517 | 2/1995 | Giuseppe | 424/60 |
| 5,518,713 | 5/1996 | Raspanti | 424/59 |

FOREIGN PATENT DOCUMENTS 0012178  6/1980  European Pat. Off. .

OTHER PUBLICATIONS

Ciba Ltd., 2-[4-(s-Triazinylamino)phenyl]benzoxazoles, CA60:14525h, 1964.

*Primary Examiner*—Mukund J. Shah
*Assistant Examiner*—Deepak A. Rao
*Attorney, Agent, or Firm*—Griffin, Butler Whisenhunt & Szipl

[57] ABSTRACT

Compounds of formula (I)

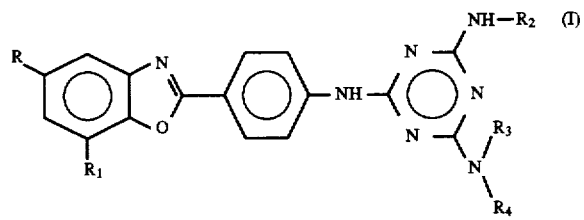

wherein the groups are as defined in the description, are useful as sunscreens in cosmetics and in the stabilization of synthetic polymers.

14 Claims, No Drawings

DERIVATIVES OF BENZOXAZOLE USEFUL AS UV FILTERS

The present invention relates to derivatives of the benzoxazole and their use in cosmetic compositions and in the stabilization of synthetic polymers.

BACKGROUND OF THE INVENTION

It is well known that sun radiations ranging from 290 to 400 nm are noxious organic materials, cutaneous tissue too. In fact, prolonged exposition to sun radiation is considered to be the main cause of the development of degenerative processes and of skin cancer forms. In particular, radiations of wavelength between 290 and 320 nm, so called UV-B radiations, cause erythema and sunburns, whose severity depends on exposure length.

It was ascertained that also the radiations ranging between 320 and 400 nm, so called UV-A, and responsible of skin tanning, can cause alterations and damages in the skin which may not be disregarded, such as for example degenerative processes and even cancer, especially in case of sensible skins or in case of prolonged exposition to radiation.

It has also been demonstrated that the UV-A radiation other than causing damages to elastin and collagen, whose consequence is ageing of the skin, can also be the cause of a number of phototoxic and photoallergic reactions. Beside, the noxious action of UV-B may be enhanced by the presence of UV-A (see: Willis et al.: Journal of Investigative Dermatology vol. 59, 416, 1072).

By means of the use of particular compounds or of compositions containing these particular compounds, so called sunscreens or UV filters, capable of absorbing, at least partially, UV sunlight radiations, noxious effects on organic materials, in particular on synthetic polymers and on human skin can be prevented or at least attenuate and ageing of the same slowed down. As protective agents a number of substances have been studied and experimented and a wide patent literature exists on this matter, in which compounds belonging to different chemical classes capable of absorbing in the UV zone of sun radiation and particularly that between 290 and 360 nm are proposed.

Many compounds, such as for example derivatives of cinnamic acid, 4-aminobenzoic acid, benzylydenecamphor, benzophenone and diphenylcyanoacrylic acid are well known and widely used in cosmetic preparations for protection from sunburns and erythema due to noxious U-VB radiation.

Until recently the use of sunscreens for the protection from the UV-A radiation was practically unknown, other than some special cases of therapy. But recent studies show that also a continuous and intensive UV-A radiation can cause severe cutaneous damages, especially to persons having very sensible and delicate skin.

For the protection against UV-A, really suitable products are not yet available, even if in the patent literature some compounds have been proposed, but in practice, the outcome of these compounds may not be considered sufficiently positive.

2-hydroxy-4-methoxybenzophenone is an often used commercial product, whose maximum absorption in the UV-A zone, at about 325 nm, is too low to give an effective protection; moreover its solubility in solvents usually used in cosmetics is very low thus making difficult its handling.

Another compound actually used in practice is a dibenzoylmethane derivative, but not only it is incompatible with many ingredients usually employed for cosmetic compositions, but also has the severe defect of not being sufficiently photostable (Int. J. Cosm. Science 10, 53 1988). Therefore the sun formulations containing these compounds may not guarantee a sufficient protection from UV-A since the sunscreens are either too weak (such as the benzophenone derivative) or are degraded too quickly by the radiation itself (such as the dibenzoylmethane derivative).

To date, therefore, it is not possible to satisfy the market requirements, since industry has not yet made available sunscreens capable of providing a sufficient protection from sunlight UV-A radiations.

SUMMARY OF THE INVENTION

It has now surprisingly been found that particular derivatives of benzoxazole have characteristics to meet the present market requirements. The derivative have good absorption, and therefore a high protective efficiency in the zone between 320 and 360 nm; they also show good photostability and wide compatibility with the ingredients usually employed in cosmetic compositions.

The compounds according to the present invention have the following formula (I):

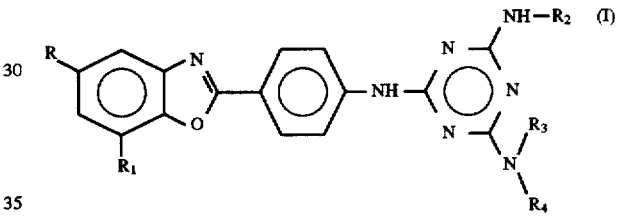

in which

R and $R_1$, which can be the same or different, are hydrogen, linear or branched $C_1$–$C_8$ alkyl; —$OR_5$ wherein $R_5$ is a $C_1$–$C_4$ alkyl; —$COOR_6$ wherein $R_6$ is linear or branched $C_1$–$C_{24}$ alkyl; $C_7$–$C_{12}$ aralkyl or $C_5$–$C_8$ cycloalkyl or a group of formula (II) or (III):

in which A is linear or branched $C_1$–$C_8$ alkyl; $C_5$–$C_8$ cycloalkyl; $C_6$–$C_{10}$ aryl, optionally substituted with one or more $C_1$–$C_4$ alkyl; $R_7$ and $R_8$ are independently hydrogen or methyl, n can have values from 1 to 10;

$R_2$ is a group of formula (IV) or (V):

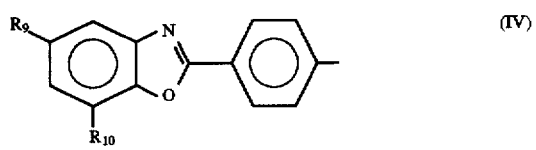

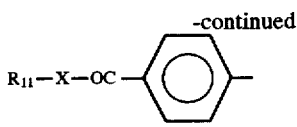

in which $R_9$ and $R_{10}$, which can be the same or different, have the same meaning of R;

$R_1$1 is linear or branched $C_1$-$C_{24}$ alkyl or a group of formula II or III;

X is oxygen or NH;

$R_3$ is linear or branched $C_1$-$C_6$ alkyl, optionally interrupted by one or more oxygen bridges; $C_6$-$C_{10}$ aryl, optionally substituted with one or more $C_1$-$C_4$ alkyls; a group of formula (III), (IV) or (V);

$R_4$ is hydrogen, linear or branched $C_1$-$C_{16}$ alkyl; or $R_3$ and $R_4$ together the nitrogen which they are linked to and optionally also to an oxygen atom form a 5-7 member heterocyclic ring, optionally substituted with $C_1$-$C_4$ alkyl groups.

DESCRIPTION OF PREFERRED EMBODIMENTS

A first group of preferred compounds comprises those wherein R, $R_1$, $R_3$ and $R_4$ have the above defined meaning and $R_2$ is the group of formula (IV).

A second group of preferred compounds comprises those wherein R and $R_1$ have the above defined meaning, $R_2$ is the group of formula (IV), $R_3$ is a linear or branched $C_1$-$C_{16}$ alkyl, $R_4$ has the same meaning of $R_3$ or is hydrogen.

A third group of preferred compounds comprises those wherein R and $R_1$ have the above defined meaning, $R_2$ is the group of formula (IV), $R_3$ is the group of formula (V) and $R_4$ is hydrogen.

A fourth group of preferred compounds comprises those wherein R and $R_1$ have the above defined meaning, $R_2$ is the group of formula (IV), $R_3$ is $C_6$-$C_{10}$ aryl, optionally substituted with $C_1$-$C_4$ alkyl, and $R_4$ is hydrogen.

A fifth group of preferred compounds comprises those wherein R, $R_1$ and $R_2$ have the above defined meaning, $R_3$ is 2,2,6,6-tetramethylpiperidin-4-yl and $R_4$ is $C_1$-$C_{16}$ alkyl, preferably $C_1$-$C_8$ alkyl, or hydrogen.

A sixth group of preferred compounds comprises those wherein R, $R_1$ and $R_2$ have the above defined meaning, $R_3$ and $R_4$, together the nitrogen which they are linked to and optionally to an oxygen atom, form a 5-7 member heterocyclic ring, optionally substituted with methyl groups.

A seventh group of preferred compounds comprises those wherein R, $R_1$ and $R_2$ have the above defined meaning, $R_3$ and $R_4$ together the nitrogen which they are linked to form a 2,2,6,6-tetramethylpiperidin-1-yl group.

An eighth group of preferred compounds comprises those wherein R and $R_1$ have the above defined meaning, $R_2$ and $R_3$ are the group of formula (V) and $R_4$ is hydrogen.

A ninth group of preferred compounds comprises those wherein R-$R_4$ have the above defined meaning, $R_{11}$ is a $C_1$-$C_{24}$ alkyl, preferably linear or branched $C_3$-$C_{20}$.

Examples of alkyl are methyl, propyl, butyl, hexyl, heptyl, octyl, decyl, dodecyl, pentadecyl, heptadecyl, eicosanyl and their branched isomers, optionally containing oxygen bridges in the form of ether groups. Particularly preferred are the groups 2-octyldodecyl, 2ethyldecyl, terbutyl, 2-ethylhexyl, 1,1,3,3-tetramethylbutyl, isobutyl.

Examples of aralkyl group are benzyl, phenylethyl, phenylpropyl, phenylhexyl, naphthylmethyl, naphthylethyl and their isomers. Aryl is phenyl and naphthyl, optional substitutions with alkyl groups, such as methyl, ethyl, isopropyl, terbutyl, can be in the orto, meta and para positions.

Examples of cycloalkyl are cyclopentyl, cyclohexyl, cyclooctyl.

Examples of heterocyclic ring are pyridine, pyrimidine, piperidine, morpholine, oxazole, optional substitutions with alkyl groups, such as methyl, isopropyl, isobutyl, terbutyl can be on the free positions of the ring, particularly preferred is the 2,2,6,6-tetramethylpiperidin-1-yl group.

The compounds according to the present invention absorb UV radiations intensely and particularly in the UV-A range, therefore small amounts of these compounds are sufficient to obtain cosmetic compositions with high SPF (Sun Protecting factor). SPF is directly related to the specific estinction and is determined in vivo on man or according to a in vitro method as described by B. Diffey J. Robson in J. Soc. Cosmet. Chem. 40, 127–133 (1989).

Moreover, the compounds of formula (I), also depending on the $R_2$-$R_4$ substituents, show a wide absorption, which is not only confined in the UV-A range, but also extended to the UV-B range. Therefore, they can provide protection against both UV-A and UV-B radiations.

It is therefore a further object of the invention the use of the compounds of formula (I) as sunscreens in cosmetic compositions and as photostabilizing agents for the protection of synthetic polymers.

In particular, it is an object of the present invention a method for protecting human skin from sunlight radiations consisting in applying on the human skin an effective amount as sunscreen of a compound of formula (I), suitably formulated in a cosmetic composition in admixture with conventional vehicle and excipients.

Another object of the present invention are cosmetic compositions containing at least a compound of formula (I).

The compounds according to the present invention can be prepared by reacting a compound of formula (VI):

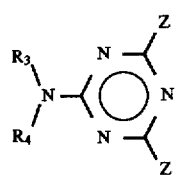

(VI)

with a compound of formula (VII):

(VII)

wherein $R_2$, $R_3$ and $R_4$ have the above defined meaning, Z is bromine or preferably chlorine.

Alternatively, a compound of formula (VIII)

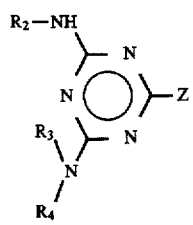

(VIII)

wherein $R_2$, $R_3$ and $R_4$ are as defined in formula (I), is reacted with a compound of formula (IX)

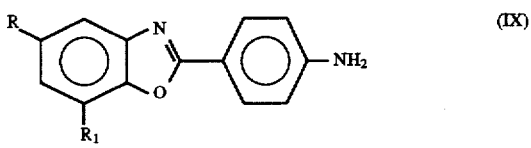

wherein R and $R_1$ are as defined in formula (I).

The intermediates of formula (VI), (VII), (VIII) and (IX) are prepared according to well-known methods available in the technical literature.

The intermediates of formula (VI) and (VIII), before the subsequent reaction with the a compound of formula (VII) and (IX) may be isolated and purified or, more easily, are reacted as raw materials, considering them as the first step of a multistep synthesis.

The reaction of the trichlorotriazine to substitute the three chlorine atoms with amino groups, same or different among them, is well-known and thoroughly described in literature, especially that relating to some classes of dyes and of optical brighteners.

The reaction between the compounds of formula VI and VIII and between those of formula VII and IX is carried out at a temperature ranging between 50° and 200° C., in suitable solvents, such as for example acetonitrile, ketones such as acetone, methylethyl ketone, ethers such as diisopropylether, tetraidrofurane, dioxane, aliphatic or aromatic hydrocarbons, such as hexane, octane, cyclohexane, benzene, toluene, xylene or mixtures thereof, optionally in the presence of an acid acceptor, such as for example alkali or alkaline-earth hydroxide, carbonates or bicarbonates of alkali metals.

The final compounds are isolated and purified according to usual methods.

According to the present invention, the compounds of formula (I) are useful as sunscreens. Their protective activity on the skin from sun radiation is carried out by applying a suitable amount on the part of the skin which is exposed to the radiations.

Suitable amounts for the applications can be determined by the skilled person in the art depending on the specific estinction coefficient $E^1_1$ of the compound of formula (I). Said coefficient is an index of the protection efficacy.

A further object of the present invention is represented by cosmetic compositions containing an effective amount of at least a compound of formula (I) as sunscreen in combination with conventional vehicles and excipients. Said compositions can be of different types, for example in the form of solutions, lotions, water-in-oil or oil-in-water emulsions; or also in the form of gels, lipsticks, aerosols.

The compositions according to the present invention can be prepared by admixing conventional ingredients, vehicles and excipients such as oils, fats, emollients, hydrating agents, moisturizing agents, softening agents, preservatives, surfactants, thickening agents, antifoam, perfumes, pigments, dyes and other else such as alcohols, polyols, electrolytes, silicone derivatives. The most commonly used solvents are triglycerides of caprinic or caprilic acid, castor oil, esters of fatty acids with isopropanol, propylene glycol, glycerin, propylene glycole-monomethyl or monoethyl or monobutyl ether.

The present invention also comprises a method for protecting cosmetics from UV radiation by adding a sufficient amount of the compounds of formula (I). In this case it is the composition whose ingredients can undergo unwanted degradation or colouring due to light to be protected from radiation induced-degradation. Such a composition may be for example hair shampoos and lacquers, hairdress lotions, hair-dye compositions, formulations for make-up, such as nail lacquers, foundation, and lipstick. Preferred cosmetic compositions are those for the protection of human skin from sun radiations. A skilled person shall be able to determine the sufficient amount of compound of formula (I) to add to a cosmetic composition in order to protect it from photodegradation.

For the purpose of protecting human skin from sunburns, the cosmetic compositions according to the present invention can contain one or more compounds of formula (I), in an amount comprised from 0.1 to 20%, preferably from 0.5 to 15% by weight with respect to the total weight of the composition. Other than compounds of formula (I), the claimed compositions can contain in combination also other sunscreens and particularly those having a maximum absorption comprised from 290 to 320 nm.

In such a manner, a protection both towards UV-A and UV-B radiations can be obtained.

Well known sunscreens, which can be combined with the compounds of formula (I) are for example: 3-(4-methylbenzylydene)-camphor; 2-ethylhexyl-(4-dimethylamino)benzoate, 2-ethylhexyl-4-methoxycinnamate, menthyl salicylate, 2-hydroxy-4-methoxybenzophenone, 2,4,6-trianilino-(p-carbo-2-ethylhexyloxy)-1,3,5-triazine, 4(1,1-dimethylethyl)-4'-methoxydibenzoylmethane, triazine derivatives disclosed in EP 0570838, 2-ethylhexyl-2cyano-3,3-diphenyl acrylate, salts of 2-phenyl-benzimidazol-5-sulfonic acid or of 2-hydroxy-4-methoxybenzophenone-5-sulfonic acid. The application of sunscreens according to the present invention can be carried out by means of cosmetic compositions containing one or more compounds of formula (I), optionally combined with one or more well-known sunscreens, such as those above cited.

It is understood that the above list of sunscreens which may be combined with the sunscreens of formula (I) is not intended to be limited, but may be expanded by the skilled person.

The cosmetic compositions according to the present invention may contain also inorganic pigments, commonly used in cosmetics, such as for example those used for the protection of human skin from UV radiations, for example titanium, zinc, silicon or aluminium oxides.

In another aspect, the present invention also provides a method for stabilizing a synthetic polymer against sunlight induced-degradation comprising adding an effective amount of at least a compound of formula (I), optionally in combination with other well-known stabilizing agents and additives for polymers.

According to the present invention as a polymeric material, which can be protected from UV radiation, it is intended polyethylene, polypropylene, polystyrene, polybutadiene, polyisoprene and their copolymers, polyvinyl acetate and its copolymers, particularly with polyethylene, polyesters such as polyethylene terephthalate, polyamides such as Nylon 6 and Nylon 6.6, polyurethanes, polyacrylates, polymethacrylates, polyvinyl chloride.

The compounds of formula (I) can be incorporated in polymers to be stabilized by means of any known method for mixing or blending additives to polymeric materials; for example, they can be mixed with the polymer in a suitable blender or mixer, or added in the form of solution or suspension in a suitable solvent such as methanol, ethanol, acetone, chloroform, then removing the solvent after mixing with the polymer, which can be in the form of powder, granulate or suspension or finally can be added to the polymer during the preparation of the same, for example in the last step of preparation.

The compounds of formula (I) can be also used in combination with other stabilizing agents and additives generally used for polymers, such as for example phenol-based antioxydants, phosphites, hindered amines and particularly those containing in their structure the 2,2,6,6-tetramethylpiperidine group, other types of UV-absorbers based on benzotriazoles or benzophenones, plastifiers, lubricants, antistatic agents, flame retardants, titanium oxide.

The amount of compounds of formula (I) necessary to an effective stabilization of the polymer depends on different factors, such as the kind and the characteristics of the polymer, the use to which it is intended, the intensity of the radiation, the duration of exposure and the presence, if any, of other stabilizing agents.

Generally, an amount comprised from 0.01 to 5% by weight of the polymer, preferably from 0.05 to 2% is sufficient, but it is understood that a skilled technician in the field shall be able to find a suitable amount.

The following examples further illustrate the invention.

EXAMPLE 1

185.5 g of p-nitrobenzoyl chloride were added to 109 g of o-aminophenol in 1,000 ml of xylene.

The so obtained suspension was slowly warmed up to 130° C. Developing hydrochloric acid was neutralized sending it to a NaOH solution.

After HCl development finished (after about 1 hour), 9.5 g of p-toluenesulfonic acid were added to the reaction mixture and stirring was continued at reflux for about 3 hours, while azeotropically distilling and collecting reaction water. After cooling at 60° C., filtering, several washings with acetone and drying, 225 g of 2-(p-nitrophenyl) benzoxazole were obtained in the form of a creamish colored substance. This substance was loaded together with 1,400 ml of ethylene glycol monomethylether and 2 g of 5% Pt/C in autoclave, washed 2–3 times with nitrogen then with hydrogen.

Subsequently, hydrogen was introduced to reach a pressure of 10 atm and the temperature was slowly raised to 90° C. while stirring. Stirring was continued at 80°–90° C. 90° C. until the absorption of hydrogen had ceased, keeping the pressure between 10 and 15 atm.

After cooling, the overpressure was discharged, the reaction mixture was washed with nitrogen.

The catalyst was filtered off from the solution, which was then vacuum-evaporated to dryness. The residue was crystallized from toluene with addition of decoloring earth. 170 g of 2-(p-aminophenyl)benzoxazole with m.p. of 176°–179° C. were obtained.

EXAMPLES 2–5

Similarly to the procedure described in Example 1 the benzoxazoles of formula (IX) listed in Table 1 below were prepared.

TABLE 1

(IX)
[structure of benzoxazole with $R$, $R_1$ substituents and $NH_2$ group]

| Example | R | $R_1$ | m.p. °C. |
|---|---|---|---|
| 2 | $CH_3$— | H | 191–193 |
| 3 | $(CH_3)_3C$— | H | 167–168 |
| 4 | $(CH_3)_3C$— | $(CH_3)_3C$— | 168–169 |
| 5 | $C_4H_9$—CH—$CH_2$OOC— $\|$ $C_2H_5$ | H | 91–93 |

EXAMPLE 6

18.5 g of sodium bicarbonate were added to a solution of 36.9 g of trichlorotriazine in 450 ml of acetone, cooled at 0° C., subsequently 51.1 g of 2ethylhexyl-p-aminobenzoate were slowly added keeping the temperature at 0° C. by cooling. Successively, the mixture was stirred for 0.5 hours, then 120 ml of water were added and stirring was continued for a further 0.5 hours, then the formed precipitate was filtered, washed several times firstly with water, then with cold acetone and vacuum-dried. 78.3 g of dichlorotriazine derivative of formula (X)

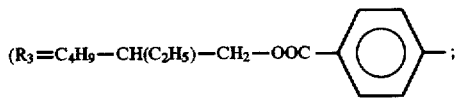

$(R_3=C_4H_9—CH(C_2H_5)—CH_2—OOC$ $R_4=H)$ were obtained in the form of a white solid with m.p. of 245°–248° C.

EXAMPLES 7–21

In a similar manner as in Example 6 the compounds of formula (X) listed in Table 2 below were prepared.

TABLE 2
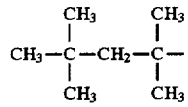
(X)
| Example | R3 | R4 | M.P. (°C.) |
|---|---|---|---|
| 7 | 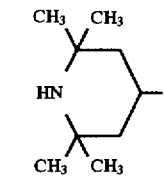 | H | 70-72 |
| 8 | 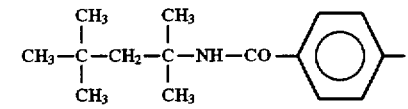 | C₄H₉ | 63-65 |
| 9 | C₁₂H₂₅— | H | 60-62 |
| 10 | 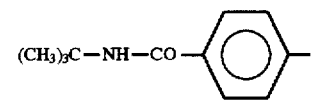 | H | 240-243 |
| 11 | (CH₃)₃C—NH—CO—⌬— | H | >250 |
| 12 | 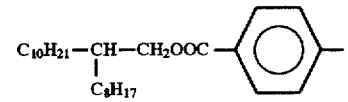 | H | 177-179 |
| 13 | 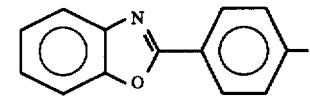 | H | >250 |
| 14 | 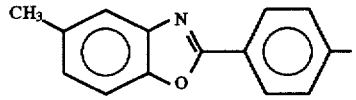 | H | >250 |
| 15 | 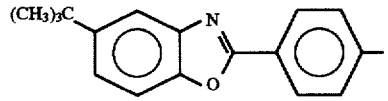 | H | >250 |
| 16 | 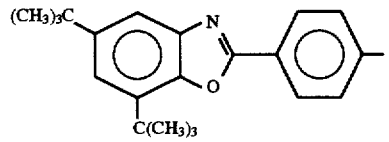 | H | 232-235 |
| 17 | 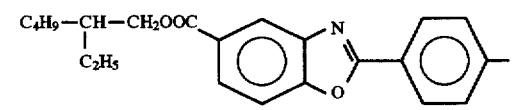 | H | 208-210 |
| 18 | 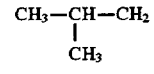 | 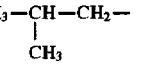 | >250 |
| 19 | (CH₃)₃C | H | 128-130 |

TABLE 2-continued

Structure (X):

R3\\N(R4)—[triazine with two CH2Cl groups]

| Example | R3 | R4 | M.P. (°C.) |
|---|---|---|---|
| 20 | C6H5— (phenyl) | H | 134–137 |
| 21 | $C_4H_9-CH(C_2H_5)-CH_2-$ | $C_4H_9-CH(C_2H_5)-CH_2-$ | >250 |

EXAMPLE 22

19.8 g of dichlorotriazine derivative of Example 6 and 23 g of benzoxazole derivative of Example 1 in 250 ml of xylene were stirred under reflux for 8 hours in nitrogen stream. Developing hydrochloric acid was sent to a NaOH diluted solution. Xylene was distilled off and the residue was crystallized from a mixture of methanol and ethylene glycol monomethyl ether. 20 g of compound of the following formula with m.p. of 215°–217° C. and $E^1_1$ of 1594 at 337 nm were obtained.

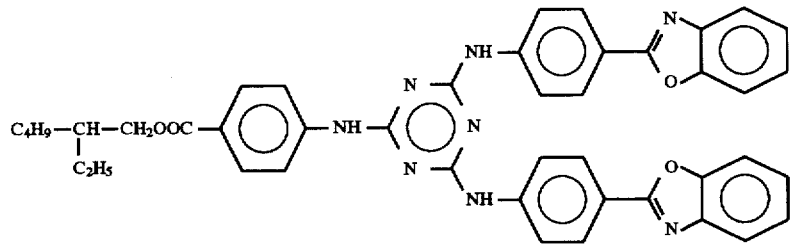

EXAMPLES 23–44

Similarly to what described in Example 22, by reacting a compound of formula (IX) with one of formula (X) the compounds of formula (XI) listed in Table 3 below were obtained.

TABLE 3

(XI)

| Example | R | R1 | R3 | R4 | M.P. (°C.) | $E_1^1$ | nm |
|---|---|---|---|---|---|---|---|
| 23 | H | H | 4-CH₃-C₆H₄ group with C₁₀H₂₁—CH(C₈H₁₇)—CH₂—OOC— substituent | H | 179–181 | 1311 | 336 |
| 24 | (CH₃)₃C— | H | 4-CH₃-C₆H₄ group with C₄H₉—CH(C₂H₅)—CH₂OOC— substituent | H | 187–190 | 1333 | 337 |
| 25 | (CH₃)₃C— | H | 4-CH₃-C₆H₄ group with (CH₃)₃C—NH—CO— substituent | H | >250 | 1479 | 337 |
| 26 | (CH₃)₃C— | (CH₃)₃C— | 4-CH₃-C₆H₄ group with benzoxazole substituent [(CH₃)₃C, (CH₃)₃C] | H | >250 | 1548 | 340 |
| 27 | (CH₃)₃C— | (CH₃)₃C— | 4-CH₃-C₆H₄ group with C₄H₉—CH(C₂H₅)—CH₂OOC— substituent | H | 225–228 | 1208 | 337 |
| 28 | (CH₃)₃C— | H | 4-CH₃-C₆H₄ group with C₁₀H₂₁—CH(C₈H₁₇)—CH₂—OOC— substituent | H | 150–153 | 1192 | 336 |

TABLE 3-continued (XI structure shown: bis-benzoxazole triazine with R, R1 on benzoxazole rings and NR3R4 on triazine)

| Example | R | R1 | R3 | R4 | M.P. (°C.) | $E_1^1$ | nm |
|---|---|---|---|---|---|---|---|
| 29 | $C_4H_9-CH(C_2H_5)-CH_2OOC-$ | H | $CH_3-C(CH_3)_2-CH_2-C(CH_3)_2-NH-CO-$ (p-phenyl) | H | 241–243 | 1147 | 337 |
| 30 | $C_4H_9-CH(C_2H_5)-CH_2OOC-$ | H | $C_4H_9-CH(C_2H_5)-CH_2OOC-$ (p-phenyl) | H | 222–223 | 1203 | 336 |
| 31 | $C_4H_9-CH(C_2H_5)-CH_2OOC-$ | H | 2-phenyl-benzoxazol-5-yl with $C_4H_9-CH(C_2H_5)-CH_2OOC-$ | H | >250 | 1023 | 336 |
| 32 | $(CH_3)_3C-$ | $(CH_3)_3C-$ | $(CH_3)_3C-NH-CO-$ (p-phenyl) | H | 192–193 | 1631 | 336 |
| 33 | H | H | $(CH_3)_3C-NH-CO-$ (p-phenyl) | H | 191–194 | 1631 | 336 |
| 34 | $CH_3$ | H | $(CH_3)_3C-NH-CO-$ (p-phenyl) | H | >250 | 1548 | 337 |

TABLE 3-continued

Structure (XI): Bis-benzoxazolyl-phenyl-amino-triazine with substituents R, R₁, R₃, R₄.

| Example | R | R1 | R3 | R4 | M.P. (°C.) | $E_1^1$ | nm |
|---|---|---|---|---|---|---|---|
| 35 | $(CH_3)_3C-$ | H | $CH_3-C(CH_3)_2-CH_2-C(CH_3)_2-CH_3$ | H | 143–145 | 1433 | 338 |
| 36 | H | H | $CH_3-C(CH_3)_2-CH_2-C(CH_3)_2-CH_3$ | H | 196–198 | 1594 | 337 |
| 37 | $CH_3$ | H | $CH_3-C(CH_3)_2-CH_2-C(CH_3)_2-CH_3$ | H | 232–233 | 1562 | 338 |
| 38 | $(CH_3)_3C-$ | H | $CH_3-CH-CH_2-$ (with CH₃) | $CH_3-CH-CH_2-$ (with CH₃) | >250 | 1547 | 340 |
| 39 | $(CH_3)_3C-$ | H | $(CH_3)_3C-$ | H | 158–162 | 1482 | 338 |
| 40 | $C_4H_9-CH(C_2H_5)-CH_2OOC-$ | H | $(CH_3)_3C-$ | H | 193–194 | 1219 | 341 |
| 41 | $CH_3$ | H | 2,2,6,6-tetramethyl-4-methylpiperidinyl | $C_4H_9$ | >250 | 1435 | 339 |

TABLE 3-continued
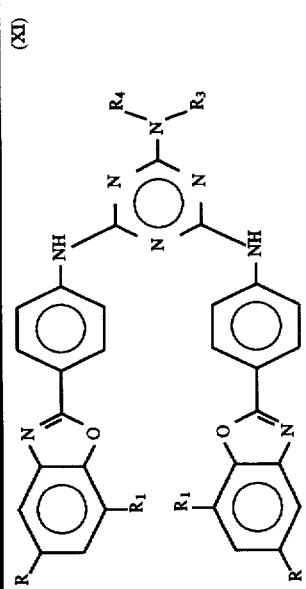
(XI)
| Example | R | R1 | R3 | R4 | M.P. (°C.) | $E_1^1$ | nm |
|---|---|---|---|---|---|---|---|
| 42 | H | H | C$_4$H$_9$—CH(C$_2$H$_5$)—CH$_2$ | C$_4$H$_9$—CH(C$_2$H$_5$)—CH$_2$ | 149–151 | 1483 | 338 |
| 43 | (CH$_3$)$_3$C— | H | C$_6$H$_5$— | H | 166–168 | 1556 | 338 |
| 44 | (CH$_3$)$_3$C— | H | CH$_3$—O—(CH$_2$)$_3$— | H | 139–141 | 1501 | 338 |

EXAMPLES 45–49

Analogously as described in Example 22, from compounds of formula (X) and 2-ethylhexyl-p-aminobenzoate the products of formula (XII) listed in Table 4 below were obtained.

TABLE 4

[Structure of formula (XII): benzoxazole with R and $R_1$ substituents, connected through phenyl-NH to a triazine bearing two NH-phenyl-COOCH$_2$-CH(C$_2$H$_5$)-C$_4$H$_9$ groups]

| Example | R | $R_1$ | M.P. °C. | $E_1^1$ | nm |
|---|---|---|---|---|---|
| 45 | H | H | 104–105 | 1373 | 314 |
| 46 | CH$_3$— | H | 162–163 | 1318 | 314 |
| 47 | (CH$_3$)$_3$C— | H | 121–123 | 1257 | 314 |
| 48 | (CH$_3$)$_3$C— | (CH$_3$)$_3$C | 110–112 | 1167 | 313 |
| 49 | C$_4$H$_9$CH(C$_2$H$_5$)—CH$_2$OOC— | H | 165–167 | 1115 | 314 |

Example A—Sun cream

| | |
|---|---|
| Polyglycole (Arlacel 165 ICI) | 2.0 g |
| Glycerine monostearate | 4.0 g |
| Benzoate of C$_{12}$-C$_{15}$ alcole | 5.0 g |
| Cetylstearyl alcohol | 3.0 g |
| Mirystic alcohol with 3 moles of propylene oxide (Witcamol APM-Witco) | 29.0 g |
| Compound of the example 25 | 2.0 g |
| 2-ethylhexyl-4-dimethylaminobenzoate | 2.5 g |
| Perfume | 0.3 g |
| Distilled water q.s. | 100 g |

The fatty phase was warmed to 80°–90° C., the compound of Example 25 was added, then the mixture was added to water, containing the hydrosoluble compounds, heated to 80°–90° C. Warm-stirring was continued for 15–20 minutes.

After slow cooling perfume was added.

Example B—Sun-milk

| | |
|---|---|
| Fatty acid Triglycerides | 20.0 g |
| Cetylstearyl alcohol | 2.0 g |
| Lanoline | 4.0 g |
| Cetyl alcohol | 2.0 g |
| Siliconic oil | 0.4 g |
| Compound of Example 48 | 3.5 g |
| Abiol (preservative by 3V SIGMA) | 0.2 g |
| Synthalen M (thickening agent by 3V-Sigma) | 0.1 g |
| Triethanol amine | 0.15 g |
| Perfume | 0.3 g |
| Distilled water q.s. | 100 g |

The preparation was carried out as in Example A.

Example C—Day-cream

| | |
|---|---|
| C$_8$–C$_{12}$ acid triglycerides | 29.8 g |
| Glycerol monostearate | 7.0 g |
| Stearic Acid | 2.0 g |
| Lanoline | 4.0 g |
| Preservative | 0.2 g |
| Compound of Example 40 | 2.0 g |
| Propylene glycole | 2.5 g |
| Triethanolamine | 0.5 g |
| Perfume | 0.3 g |
| Distilled water q.s. | 100 |

The composition was prepared as described in Example A.

Example D—Alcoholic gel

| | |
|---|---|
| Propylene glycol | 25.0 g |
| Ethyl alcohol | 25.0 g |
| Synthalen M (thickening agent by 3V-SIGMA) | 0.6 g |
| Compound of Example 29 | 2.5 g |
| Triethanolamine | 0.3 g |
| Preservative | 0.3 g |
| Perfume | 0.3 g |
| Distilled water q.s. | 100 |

Synthalen M was dispersed in water, then triethanolamine, preservative, propylene glycole and ethanol mixture, wherein the compound of Example 29 was previously dissolved, was added, perfume was last added.

Example E

Lipstick

A base mixture was first prepared consisting of:

| | |
|---|---|
| Beeswax | 13.0 g |
| Carnauba wax | 7.5 g |

-continued

| | |
|---|---|
| Lanoline | 5.0 g |
| Isopropyl miristate | 8.0 g |
| Mineral oil | 3.0 g |
| Castor oil | 63.5 g |

85 g of this mixture were warmed up to melt, to the molten mass 5 g of compound of the Example 1 and 8 g of 3-(4-methylbenzylyden)camphor were added, as well as perfume, flavors and dyes, then it was diluted to 1,000 g with castor oil and cooled to room temperature.

Example F 1000 g of low density polyethylene (Riblene EF 2100 R Enichem), 2 g of n-octadecyl-3-(3,5-di-terbutyl-4hydroxyphenyl) propionate, 1 g of calcium stearate and 0.3 g of a compound of formula (I) were homogeneously mixed. The obtained mixtures were extruded at 190° C. and transformed into granules. From these, by pressing at 200° C., films of 0.2 mm were obtained.

Samples of these films were subjected to UV radiations in a Weatheromether WOM Ci-65 at a black panel temperature of 63° C. In the irradiated samples, the increase of the carbonylic band at 5.85 nm in infrared field was measured and T-0.1, i.e. the time necessary to achieve an increase of 0.1 of the carbonylic band was determined and compared with a film which did not contain stabilizing agents of formula (I). The results are reported in the Table 5.

TABLE 5

| Stabilizing agent (Hours) | T 0.1 |
|---|---|
| No agent | 340 |
| Compound of Example 46 | 1170 |
| Compound of Example 41 | 1280 |
| Compound of Example 49 | 960 |

We claim:
1. Compounds of formula (I):

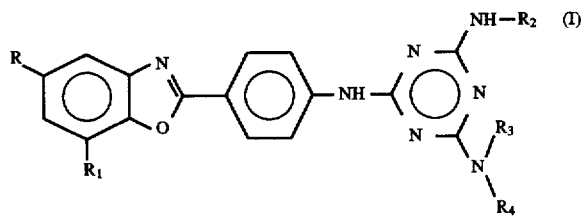

in which

R and $R_1$, which can be the same or different, are hydrogen, linear or branched $C_1$–$C_8$ alkyl; —$OR_5$ wherein $R_5$ is a $C_1$–$C_4$ alkyl; —$COOR_6$ wherein $R_6$ is linear or branched $C_1$–$C_{24}$ alkyl; $C_7$–$C_{12}$ aralkyl or $C_5$–$C_8$ cycloalkyl or a group of formula (II) or (III):

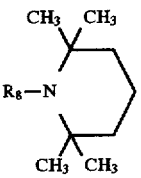

in which A is linear or branched $C_1$–$C_8$ alkyl; $C_5$–$C_8$ cycloalkyl; $C_6$–$C_{10}$ aryl, optionally substituted with one or more $C_1$–$C_4$ alkyl; $R_7$ and $R_8$ are independently hydrogen or methyl, n can have values from 1 to 10;

$R_2$ is a group of formula (IV) or (V):

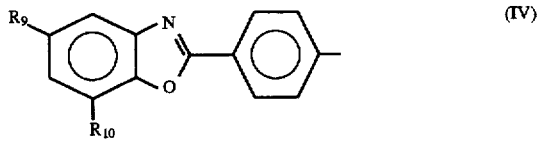

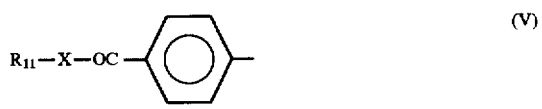

in which $R_9$ and $R_{10}$, which can be the same or different, have the same meaning of R;

$R_{11}$ is linear or branched $C_1$–$C_{24}$ alkyl or a group of formula II or III;

X is oxygen or NH;

$R_3$ is linear or branched $C_1$–$C_{16}$ alkyl, optionally interrupted by one or more oxygen bridges; a group of formula (III), (IV) or (V);

$R_4$ is hydrogen, linear or branched alkyl $C_1$–$C_{16}$; or $R_3$ and $R_4$ together with the nitrogen which they are linked to and optionally also to an oxygen atom form a 5–7 member heterocyclic ring, optionally substituted with $C_1$–$C_4$ alkyl groups.

2. Compounds according to claim 1, wherein R, $R_2$ is the group of formula (IV).

3. Compounds according to claim 1, wherein $R_2$ is the group of formula (IV), and $R_3$ is a linear or branched $C_1$–$C_{16}$.

4. Compounds according to claim 1, wherein $R_2$ is the group of formula (IV), $R_3$ is the group of formula (V) and $R_4$ is hydrogen.

5. Compounds according to claim 1, wherein $R_2$ is a group of formula (IV), and $R_4$ is hydrogen.

6. Compounds according to claim 1, wherein $R_3$ is 2,2,6,6-tetramethylpiperidin-4-yl.

7. Compounds according to claim 1, wherein $R_3$ and $R_4$ together with the nitrogen which they are linked to and optionally with oxygen form a 5–7 member heterocyclic ring substituted with methyl groups.

8. Compounds according to claim 1, wherein $R_3$ and $R_4$ together with nitrogen which they are linked to form a 2,2,6,6-tetramethylpiperidin-1-yl group.

9. Compounds according to claim 1, wherein $R_2$ and $R_3$ are the group of formula (V) and $R_4$ is hydrogen.

10. Compounds according to claim 1, wherein $R_{11}$ is a linear or branched $C_3$–$C_{20}$ alkyl.

11. A method for protecting human skin from sunlight radiations consisting in applying on the human skin an effective amount as sunscreen of a compound according to claim 1, formulated in a cosmetic composition in admixture with conventional vehicle and excipients.

12. A cosmetic or dermatologic composition containing one or more compounds of claim 1 in amount from 0.1 to 20% by weight with respect to the composition.

13. A cosmetic or dermatologic composition according to claim 12, further containing well-known sunscreens.

14. A composition according to claim 13, wherein said well-known sunscreen is selected from the group consisting of 3-(4-methylbenzylydene)-camphor; 2-ethylhexyl-(4-dimethylamino)benzoate, 2-ethylhexyl-4-methoxycinnamate, menthyl salicylate, 2-hydroxy-4-methoxybenzophenone, 2,4,6-tri-anilino-(p-carbo-2-ethylhexyloxy)-1,3,5-triazine, 4-(1,1-dimethylethyl)-4'-methoxydibenzoylmethane, 2-ethylhexyl-2-cyano-3,3-diphenyl acrylate, salts of 2-phenyl-benzimidazol-5-sulfonic acid or of 2-hydroxy-4-methoxy-benzophenone-5-sulfonic acid.

* * * * *